(12) United States Patent
Alouani et al.

(10) Patent No.: US 7,028,723 B1
(45) Date of Patent: Apr. 18, 2006

(54) APPARATUS AND METHOD FOR AUTOMATIC PRESCRIPTION VERIFICATION

(76) Inventors: Ali Tahor Alouani, 925 Wyleswood Dr., Cookville, TN (US) 38501; Kenneth R. Currie, 3643 Shenandoah La., Cookeville, TN (US) 38506

( * ) Notice: Subject to any disclaimer, the term of this patent is extended or adjusted under 35 U.S.C. 154(b) by 0 days.

(21) Appl. No.: 10/979,474

(22) Filed: Nov. 2, 2004

Related U.S. Application Data (60) Provisional application No. 60/516,176, filed on Nov. 3, 2003.

(51) Int. Cl.
*B65B 1/04* (2006.01)

(52) U.S. Cl. .................. 141/83; 141/94; 702/128
(58) Field of Classification Search ........... 141/83, 141/94, 104; 221/129, 219; 702/128, 129
See application file for complete search history.

(56) References Cited

U.S. PATENT DOCUMENTS

| | | | | |
|---|---|---|---|---|
| 5,439,036 A | * | 8/1995 | Kramer | 141/1 |
| 5,502,944 A | * | 4/1996 | Kraft et al. | 53/55 |
| 5,765,606 A | * | 6/1998 | Takemasa et al. | 141/104 |
| 6,535,637 B1 | * | 3/2003 | Wootton et al. | 382/190 |
| 6,738,723 B1 | * | 5/2004 | Hamilton | 702/128 |
| 6,771,369 B1 | * | 8/2004 | Rzasa et al. | 356/326 |

* cited by examiner

*Primary Examiner*—Steven O. Douglas
(74) *Attorney, Agent, or Firm*—Jessica Costa (57) ABSTRACT

An apparatus and method are used to perform the verification of a pharmaceutical prescription after it is filled but prior to shipment. Due to the high volume of mail/internet orders, the analysis is to be performed on the whole prescription, not on each individual pill of the prescription. The apparatus automatically gathers information about the pills contained in a pill bottle, including image and weight information, and incorporates a decision-making engine to decide whether the content of the pill bottle matches the prescription order.

20 Claims, 4 Drawing Sheets

APPARATUS AND METHOD FOR AUTOMATIC PRESCRIPTION VERIFICATION

This application claims the benefit of 60/516,176 filed Nov. 3, 2003.

BACKGROUND OF THE INVENTION

Prescriptions for pharmaceuticals are now commonly and increasingly being placed via mail-order and over the internet. In order to meet high volume prescription demand in a timely manner, the process of filling prescriptions has been highly automated, especially at large mass production prescription fill facilities.

Generally speaking, prescription orders are now processed by computer. The computer generates a prescription label to be placed on a pill bottle. Pills that match the prescription are then automatically dispensed into the pill bottle.

In one arrangement, an automated prescription fulfillment system is a conveyor belt system that includes dispensing bins each containing large quantities of pills of a given type. A label station, under computer control, generates and adheres the prescription label to a pill bottle. The prescription label generally includes at least a pill identifier and a pill quantity. A conveyor belt or other transport mechanism transports the labeled pill bottle past dispensing mechanisms of pill dispensing bins that contain pills of varying types. The dispensing mechanism of the pill dispensing bin that contains pills that match the pill identifier on the prescription label automatically dispenses pills from its pill dispensing bin into the pill bottle. By design, the quantity of pills dispensed should match the pill quantity on the prescription label.

Because of the potential danger that taking unprescribed pharmaceuticals poses to the public, quality control of the filled prescriptions is of utmost concern. Accordingly, although automation often improves the output quality of a product due to the removal of human error, there still exists the possibility of prescription inaccuracy. For example, due to malfunctioning pill dispensing mechanisms, an incorrect quantity of pills may be dispensed into the pill bottle. For other reasons, for example due to computerized label reading problems, label printing problems, or human error, the dispensing bin may contain the incorrect pills or the wrong dispensing mechanism may be triggered to dispense pills, resulting in the incorrect pills in the pill bottle.

A need therefore exists for a post-fill quality control technique that verifies the accuracy of a filled prescription after the pills have been dispensed into the pill bottle. Verification of filled prescriptions by human inspection is costly and time-consuming. However, even in the automated environment, verification of each individual pill as it is dispensed into the pill bottle is costly in terms of complicated hardware and software, and time-consuming, preventing the verification of large numbers of prescriptions as required by high volume pharmaceutical mail/internet orders. Accordingly, a need also exists for an automatic post-fill quality control analysis to be performed after the entire quantity of pills have been dispensed into the pill bottle which verifies the accuracy of the filled prescription.

SUMMARY OF THE INVENTION

An apparatus and method are used to perform the verification of a pharmaceutical prescription after pills of the prescription quantity and type have been fully dispensed into a pill bottle. The apparatus is an automatic prescription verification system that automatically gathers image and weight information about the pills contained in a pill bottle filled according to prescription information. The system includes decision-making capability which determines an accuracy level of the filled prescription based on the actual image and weight data, along with expected image and weight information determined from information derived from the prescription label and known about pills of the type identified in the prescription label. The automatic prescription verification system is preferably equipped with a range sensor, a digital camera, and a scale. The pill bottle is placed in a predetermined position to allow the range sensor to measure a distance used by the camera as a focal length for adjusting the camera lens and/or position so that the image of the pill bottle taken by the camera will be in focus and of sufficient quality. The camera obtains an image of the content of the pill bottle, from which image information such as color, volume, and pill label can be determined. In the preferred embodiment, the apparatus includes a specialized image data processing engine that processes image data from the obtained image to classify the color of the content of the pill bottle into one of a plurality of different color classes and/or to classify labels on the surfaces of the pills in the pill bottle into one of a plurality of different pill type classes. The apparatus preferably also includes a fuzzy logic based decision fusion block that classifies the entire prescription into an accuracy level based on prescription color, pill label, volume, and weight classifications ultimately derived from the actual image data, weight data, and range information.

The apparatus may be beneficially employed in a conveyor belt based prescription fill system. To this end, the apparatus may be configured to implement each of the range sensor, camera, scale, and prescription accuracy decision processor at separate measurement stations in order to form a pipelined mass-production setup to eliminate unnecessary idle time by any of the measurement stations. Such an apparatus may then be positioned in the conveyor belt based prescription fill system somewhere after the pill dispenser bins to perform prescription fill quality control on each pill bottle as it passes along the line.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION

Figure 1:
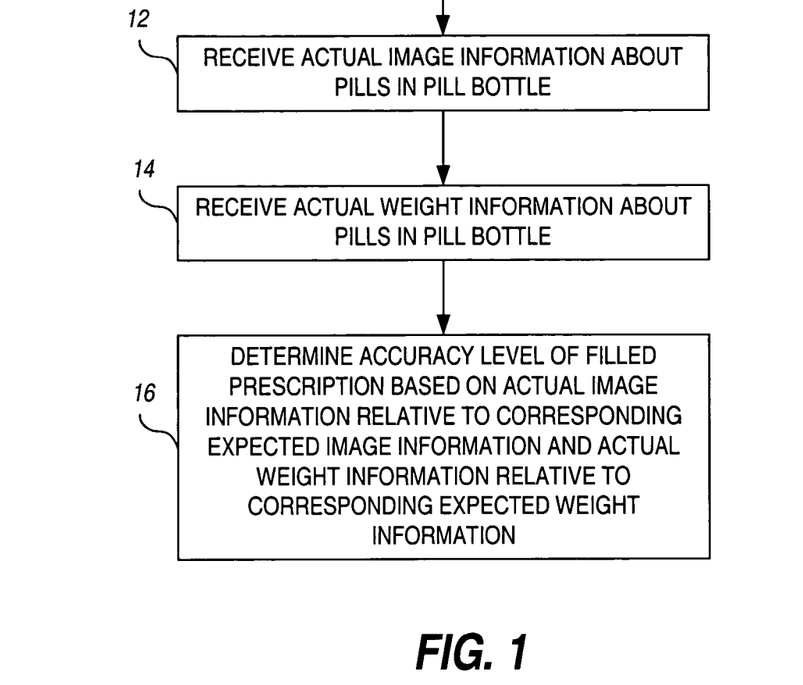
FIG. 1 is a flowchart illustrating a preferred method for verifying the accuracy of a filled prescription.

Turning now to the drawings, FIG. 1 illustrates a method in accordance with the invention for verifying the accuracy of a filled prescription of pills that are contained in a transparent or pseudo-transparent pill bottle. As illustrated therein, the method 10 includes receiving actual image information about the pills in the pill bottle (step 12). In this regard, image information about the pills may be obtained from image data acquired by a an image acquisition apparatus such as camera, an x-ray tube or other means of penetrating radiation, or other imaging apparatuses. The image information may be the actual image data (e.g., gray level, RGB (Red, Green, Blue), HSV (Hue, Saturation, Value), or HIS (Hue, Saturation, Illumination)) values of imaged pixels) or may be characteristics (e.g., pill color) or features (e.g., labels on pills, volume of pills) derived from the image and range data.

The method 10 also includes receiving actual weight information about the pills in the pill bottle (step 14). In this regard, the weight information may be the actual weight of the total number of pills and bottle combined, or the actual weight of the total number pills alone (i.e., by adjusting the actual scale measurement by the known weight of the pill bottle), or the actual average weight of a single pill (or other combinations less that the total number of pills) in the pill bottle.

The steps for receiving image information (step 12) and for receiving weight information (step 14) are not order-sensitive.

The method 10 includes determining a level of accuracy of the filled prescription based on the actual image information relative to corresponding expected image information and the actual weight information relative to corresponding expected weight information (step 16).

Figure 2:
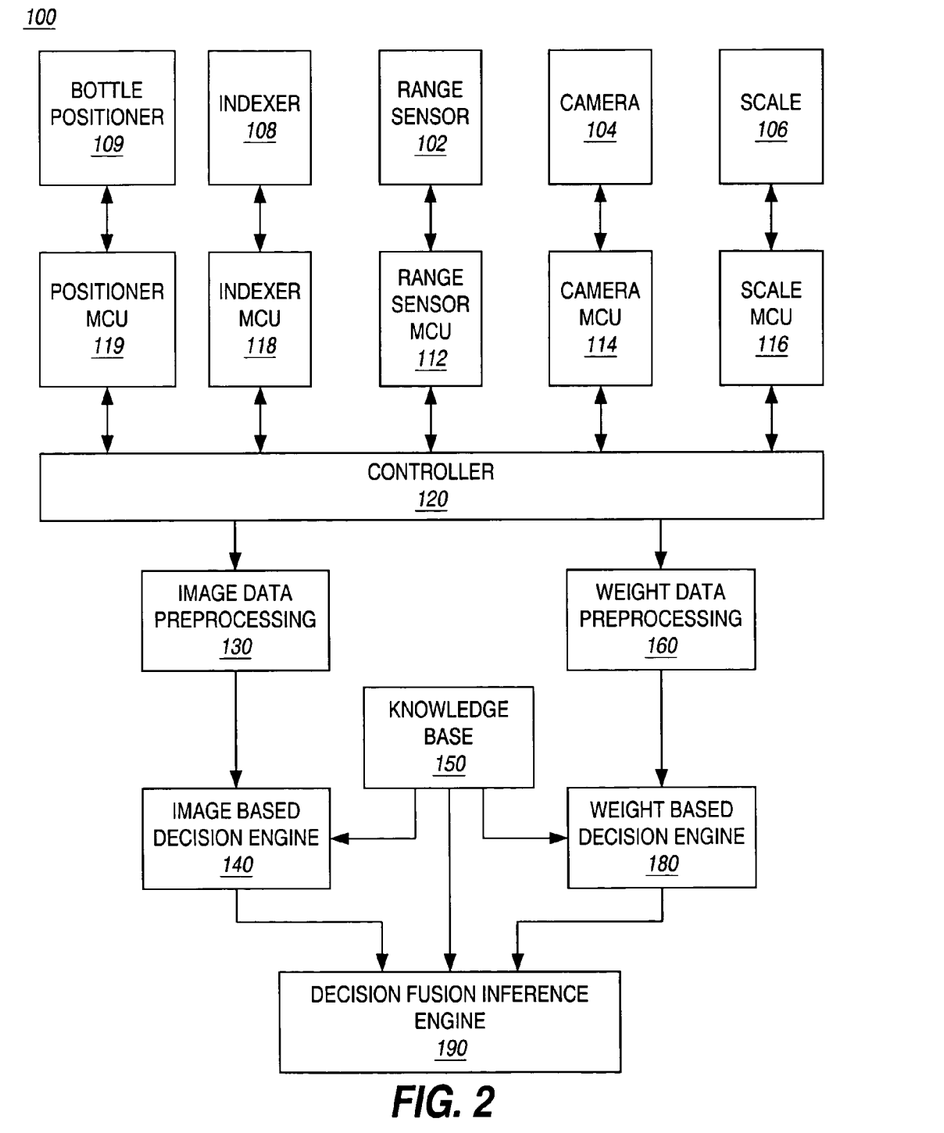
FIG. 2 is a block diagram of a preferred embodiment of an automatic prescription verification system implementing the techniques of the invention.

FIG. 2 is a block diagram of a preferred embodiment automatic prescription verification system 100 of the invention. The automatic prescription verification system 100 includes a range sensor 102, a camera 104, a scale 106, a prescription indexer 108, and a bottle positioner 109, each locally controlled by a respective micro-control unit (MCU)—range sensor MCU 112, camera MCU 114, scale MCU 116, indexer MCU 118, and bottle positioner MCU 119. A main controller 120 coordinates the actions of each of the sensors 102, 104, 106 and peripherals 108, 109 via the local controllers 112, 114, 116, 118, 119. The automatic prescription verification system 100 also includes image and weight data processing functionality 130 and 160 respectively, and decision processing functionality, including a local image based decision engine 140 and local weight based decision engine 180, and overall decision fusion inference engine 190, all of which access a knowledge base 150 containing prescription and pill information. The local sensor and peripheral controllers 112, 114, 116, 118, 119 and main controller 120 are generally implemented in hardware or hardware and software combined. The data and decision processing functionality and knowledge base 110 are generally respectfully embodied as software application and a database in a computer system.

Turning now in more detail to the automatic prescription verification system 100, the bottle positioner 109 operates to position a pill bottle in one or more predetermined positions relative to the range sensor 102, the camera 104, and the scale 106. Positioning each pill bottle in a predetermined position for each successive pill bottle measurement ensures consistency in the measuring process and in measurements taken from pill bottle to pill bottle. In the preferred embodiment, the conveyor belt based system, as discussed later, the bottle positioner 109 controls positioning of a pill bottle in at least three different predetermined positions, namely at a different predetermined position for obtaining each of the range measurement, the image data, and the weight measurement. Physical pill bottle positioning is achieved through a combination of the positioner MCU 119, mechanical actuators, and other mechanical assembly (not shown).

The range sensor 102 obtains a range measurement which is used to determine the focal length between the lens of the camera 104 and the filled pill bottle being verified. It can also be used to determine the volume occupied by the pills in the pill bottle. In the preferred embodiment, the range sensor 102 is positioned at a predetermined position above the base upon which the pill bottle is positioned, and the range measurement is actually the distance between the range sensor 102 and the top of the pill bottle when the pill bottle is positioned on the base in the predetermined position. The range sensor 108 is preferably controlled by way of the range sensor MCU 118, i.e., processor, which can be controlled to reset the sensor, calibrate the sensor, make a measurement, and/or hold the measurement.

The camera 104 obtains the image data associated with a pill bottle positioned in a predetermined position relative to the camera 104. The lens and/or height of the camera 104 is automatically adjusted, for example by way of the camera MCU 114 and one or more actuators (not shown), to focus the lens and/or position the camera 104 to obtain a focused image of the pill bottle and contents therein. In the preferred embodiment, the range measurement is used to adjust the height of the camera so that the lens of the camera is at a predetermined position relative to the top of the pill bottle. Image data obtained from the camera 104 is sent to the data and decision processing functionality, discussed hereinafter.

The scale 106 measures the weight of the pill bottle together with its contents. The scale is controlled by way of the scale MCU 116 which can be controlled to reset the scale, calibrate the scale, make a measurement, and/or hold the measurement. The weight measurement is also sent to the data and decision processing functionality.

The automatic prescription verification system 100 may be configured to automatically verify a filled pill bottle with respect to its prescription order in a production line environment. In such an environment, the automatic prescription verification system 100 requires a way to index and obtain the prescription order associated with each pill bottle it processes. The automatic prescription verification system 100 therefore preferably also includes an indexer 208 that may be controlled by way of an indexer MCU 218.

In the preferred embodiment, the prescription order is obtained directly from a prescription label adhered to the pill bottle. In one embodiment, the prescription label includes a barcode. In this embodiment, the indexer 108 comprises a bar code reader that reads the bar code on the pill bottle label. The bar code on the label maps to prescription information about the prescription order, which may be contained in the knowledge base 150 or in other computer memory, including pill type and quantity of pills.

In an alternative embodiment, the camera 104 obtains image data of the content of the pill bottle and passes it to the data and decision processing functionality. The data and decision processing functionality processes the image data and converts it to useful prescription information, for example by way of a dedicated image processing module or a neural network image character reader (not shown).

In yet another embodiment, the prescription information is provided to the data and decision processing functionality via other software, for example the software that generates the prescription label.

The data and decision processing functionality includes any necessary hardware and software for processing indexing information, range measurements, image data, and weight measurements, and for coordinating the actions of each of the indexer 108, range sensor 102, camera 104, and scale 106. The data and decision processing functionality therefore includes a main controller 120. Also, because the data coming from the sensors generally comprises raw data (e.g., gray level, RGB, HSV, or HSI pixel data from the camera 104 and digital or analog weight measurement data reflective of the weight of the pill bottle and contents combined), preprocessing of this data is generally required to convert it into the format and parameter type used by the decision making functionality in determining the accuracy level of the prescription. Accordingly, the automatic prescription verification system 100 preferably includes image data pre-processing functionality 130 and weight data pre-processing functionality 160. The image data pre-processing functionality 130 may be implemented using special pre-processing and filtering functions that comprise data transforms applied to the image data that reduce the effects of non-uniform lights, edge effects from the bottom and/or side of the bottle, etc. The weight data pre-processing functionality 160 may comprise mathematical operations applied to the weight data such as subtracting the weight of the pill bottle from the weight measurement to obtain the weight only of the contents of the pill bottle.

The automatic prescription verification system 100 includes decision processing functionality that operates to determine the accuracy of the filled prescription based on the measurements obtained from the sensors and expected measurements based on information known about the prescription and pills in the prescription. To this end, in the preferred embodiment the automatic prescription verification system 100 includes an image based decision engine 140, a weight based decision engine 180, and a knowledge base 150.

Figure 4:
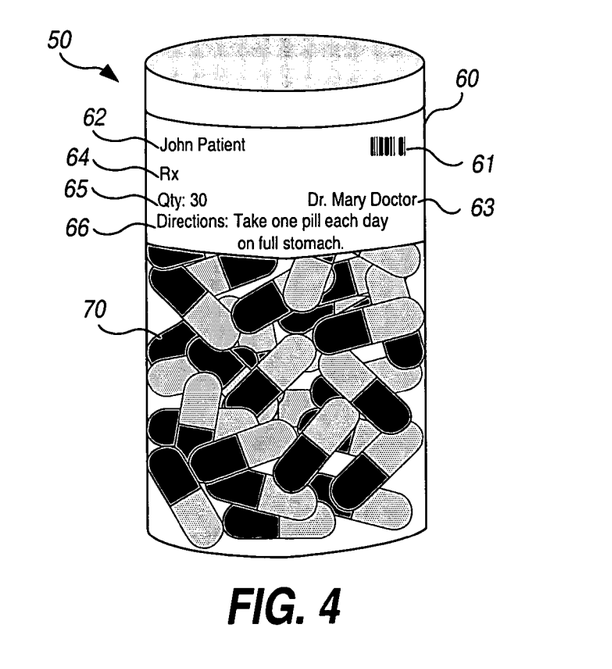
FIG. 4 is a headlong view of a labeled pill bottle filled with pills.

In order to reach any decision concerning the accuracy of the prescription, the decision processing functionality requires certain knowledge about the prescription order and about the pills comprising the prescription order. In the preferred embodiment, the prescription label provides an index in the form of a bar code that is read by the barcode reader and used to access the prescription order in a knowledge base 150. FIG. 4 illustrates a pill bottle 50 having a prescription label 60 adhered thereon and filled with a number of pills 70. The prescription label 60 includes a bar code 61 and printed information including the patient name 62, doctor name 63, name of the pills 64, quantity of pills 65, and dosage description 66. There will typically be additional prescription information printed on the label, such as patient address, company logos, etc. The prescription order is preferably stored in the knowledge base 150. The bar code 61 preferably operates as an index into the knowledge base 150 for locating the prescription order associated with the filled prescription.

The knowledge base 150 also contains additional relevant information about the pills prescribed in the prescription order that is necessary for determining the accuracy of the contents of the filled pill bottle. This information may include, for example, the average pill weight of a single pill of the type required by the prescription order, the cumulative weight of multiple pills of the type required by the prescription order, pre-defined threshold limits or margins of error or other statistical information about the pill weights, a representative pill color, any labels or other distinguishing marks or features of the pill, etc.

Based on the prescription information and other information obtained from the knowledge base 150, the data and decision processing functionality obtains, determines, and/or calculates expected image information and expected weight information that it would expect to receive from the camera 104 and scale 106 and/or that it would expect the processed image data and/or processed weight data to look like if the filled pill bottle is accurately filled. Local decision making concerning the image data is performed using an image based decision engine 140, which in the preferred embodiment is implemented as a dedicated image processing module and a neural network based learning system that classifies the color and extracted pill labels of the imaged pills in the bottle. Local decision making concerning the weight data is performed using a weight based decision engine 180, which in the preferred embodiment is implemented using a statistical classifier that classifies the collective weight of all the pills in the bottle. The data and decision processing functionality also includes a decision fusion inference engine 190 that determines a level of accuracy of the filled prescription based on the local decisions output from the local image based decision engine 140 and local weight based decision engine 180. The accuracy level may be a simple go/no-go test, where the filled pill bottle is passed as acceptable if the actual image and weight information substantially matches the expected image and weight information, or may be a more complicated classification system with two or more classes and intricate decision trees.

Figure 3:
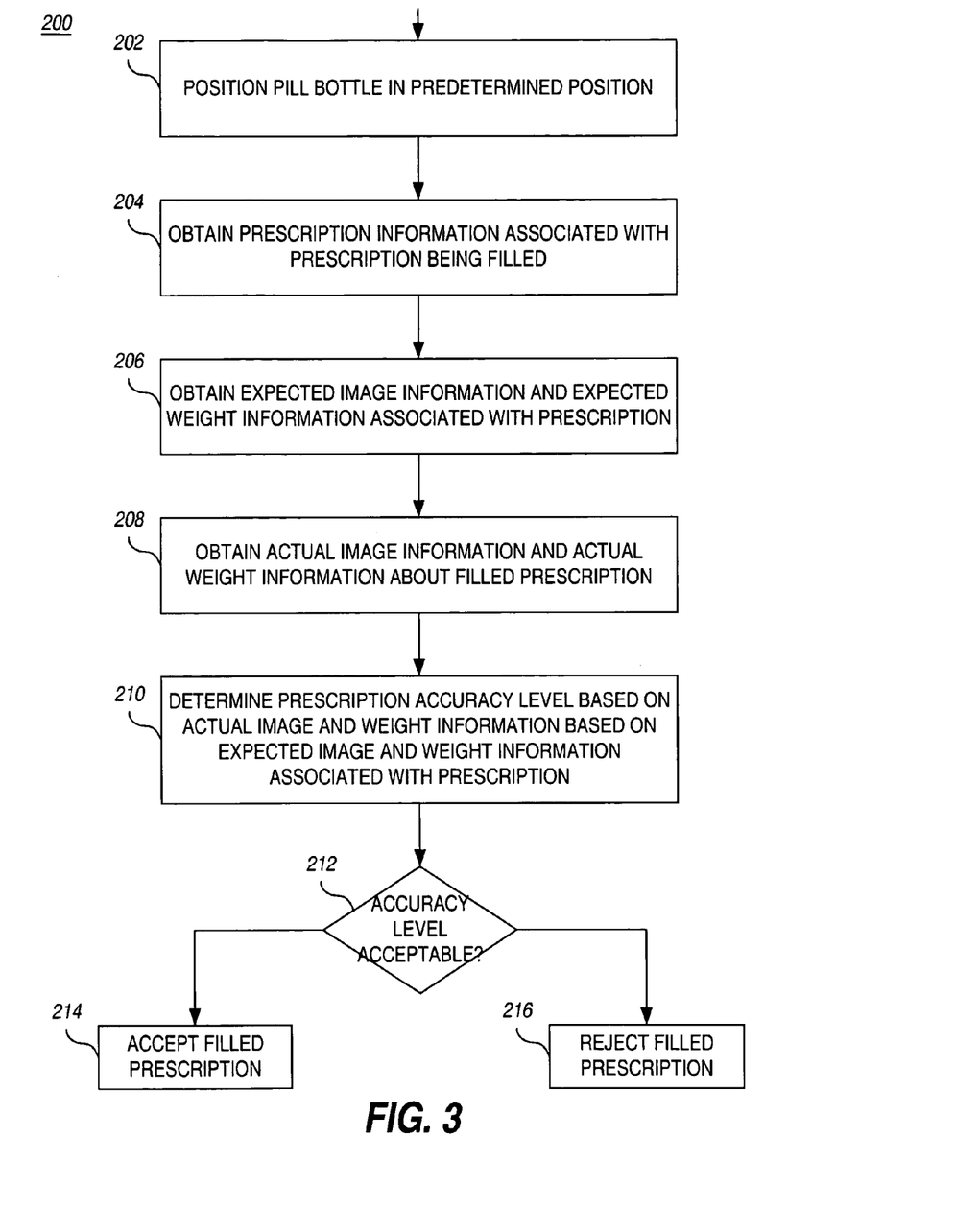
FIG. 3 is a flowchart illustrating the operation of the automatic prescription verification system of FIG. 2.

The operation of the automatic prescription verification system 100 of FIG. 2 is shown in flowchart form at 200 in FIG. 3. As shown therein, the automatic prescription verification system 100 positions a pill bottle in a predetermined position (step 202). Preferably the pill bottle comprises a prescription identifier such as a barcode. The automatic prescription verification system 100 then obtains prescription information associated with the prescription being filled, preferably through association with a prescription identifier on the pill bottle (step 204). From the prescription information, the automatic prescription verification system 100 obtains expected image information and expected weight information associated with the prescription (step 206), for example from the knowledge base 150. The automatic prescription verification system 100 obtains actual image information and actual weight information about the filled prescription of pills in the pill bottle (step 208), and determines a prescription accuracy level (step 210) based on the actual image information and actual weight information in view of the expected image information and expected weight information associated with the prescription information. Generally, if the accuracy level is acceptable (determined in step 212), for example if the actual image information is within pre-defined image tolerance limits of expected image information and the actual weight information is within pre-defined weight tolerance limits of expected weight information, the filled prescription is accepted (step 214) and can be shipped to the consumer. Otherwise the filled prescription is rejected (step 216) and must be re-filled.

Figure 5:
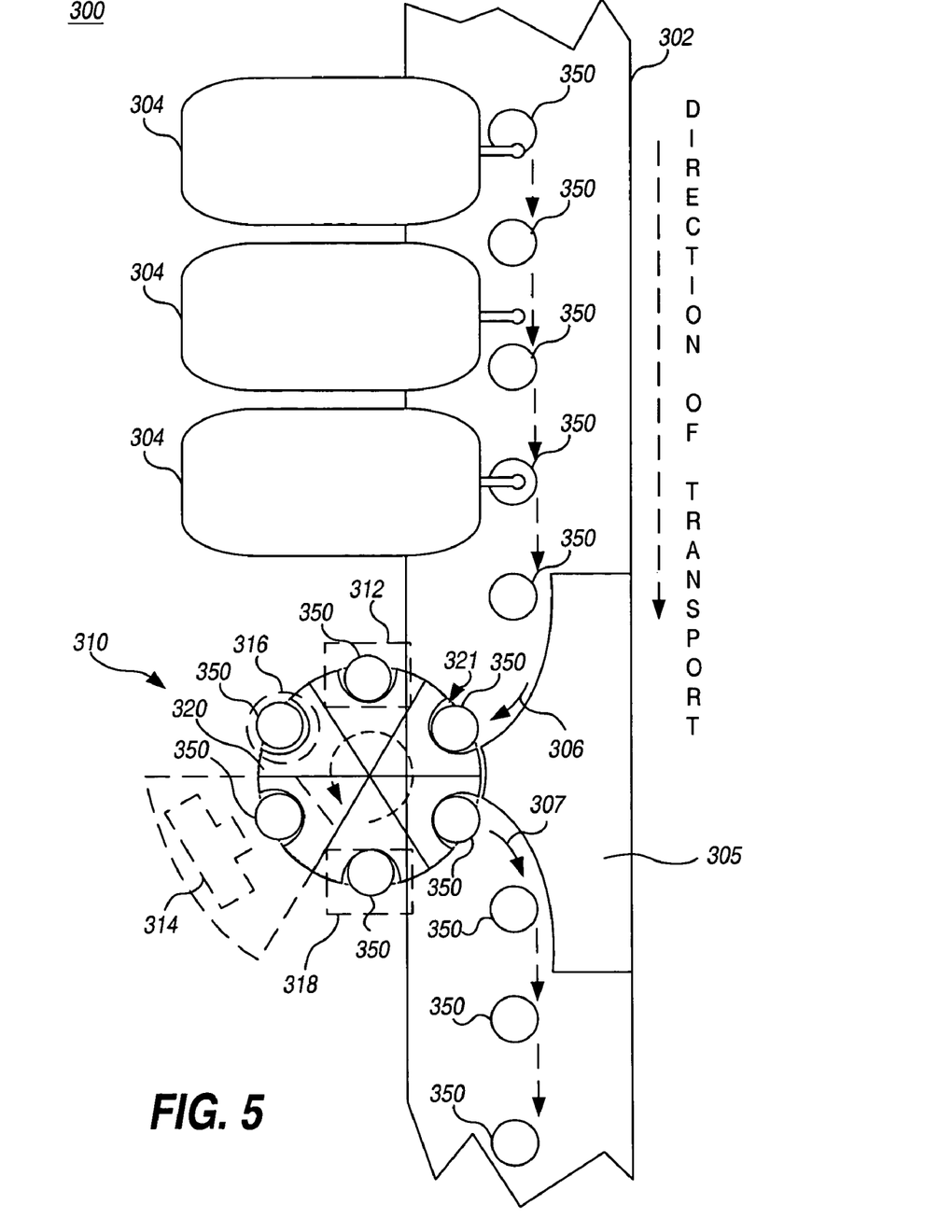
FIG. 5 is a top view of a conveyor belt prescription fill system that implements the automatic prescription verification system of the invention.

The apparatus of the invention is highly beneficial in the prescription filling assembly line environment. FIG. 5 shows a portion of a conveyor belt prescription filling production line system 300 that implements an automatic prescription verification system 310 according to the invention. In this embodiment, the automatic prescription verification system 310 is positioned along the conveyor belt 302 that transports filled pill bottles 350 from the pill dispenser bins 304 to stations further down the production line 300. The automatic prescription verification system 310 includes a rotating turn-table 320 having equally spaced nests 321 around the edges of the turn-table. The nests 321 are each large enough to accommodate the largest size pill bottle 350 used to fill prescriptions on the production line 300. A detour barrier is implemented between the entrance 306 and exit 307 of the automatic prescription verification system 310. At entrance 306, the detour barrier 305 directs each pill bottle 350 into a nest of the rotating automatic prescription verification system turn-table 320 by force of the transporting conveyor belt 302. The automatic prescription verification system 310 in this embodiment includes a range station 312, a scale station 316, and a camera station 314, which each perform their functions as discussed previously with respect to FIG. 2. The rotating turn-table 320 rotates each nest from one station to the next within the automatic prescription verification system 310. So, for example, a pill bottle 350 that has been filled at a pill dispenser bin 304, is transported by way of the conveyor belt towards the automatic prescription verification system. As the pill bottle 350 contacts the detour barrier 305 at entrance 306, the detour barrier 305 channels the pill bottle 350 into an open nest 321 in the rotating turn-table 320 of the automatic prescription verification system. The turn-table 320 rotates to bring the nest to a predetermined position relative to a range sensor 312, which obtains a range measurement associated with the pill bottle 350. The turn-table 320 then rotates again to bring the nest to a predetermined position on a scale 316, where a weight measurement is obtained. The turn-table 320 then rotates again to bring the nest to a predetermined position relative to a camera 314, where image data is obtained. The turn-table 320 then rotates again, where a decision system 318 determines whether the contents of the pill bottle 350 meet a minimum threshold of accuracy requirements. If the decision processor determines that the contents of the pill bottle 350 are accurate, the pill bottle 350 is channeled out of the automatic prescription verification system 310 on the next rotation of the turn-table 320 and onto the conveyor belt 302 at exit 307, where it is transported further down the production line 300.

If the decision processor 318 determines that the contents of the pill bottle 350 do not meet the minimum level of accuracy, the pill bottle 350 is removed from the production line in order to be refilled. Functionality for this operation may be implemented according to one of various methodologies. In one embodiment, the decision making station in the automatic prescription verification system 100 includes a robotic arm (not shown) that has the ability to grasp a rejected pill bottle and remove it from the nest and deposit it into a reject depository or other facility for re-entry into the system for refill. In an alternative embodiment, the pill bottle 350 is channeled out of the automatic prescription verification system 310 on the next rotation of the turn-table 320 and onto the conveyor belt 302 with the assistance of the exit channel 307 of the detour barrier 305, where it is transported further down the production line 300 to a reject removal station (not shown), which may be human-monitored, or may be implemented automatically. In this embodiment, the indexer is used to keep track of the pass/reject status of each pill bottle so that if rejected, it can be properly identified and removed from the accepted filled pill bottles.

The automatic prescription verification system 310 utilizes a parallel processing architecture which performs different functions at different stations. This architecture allows each sensor/decision station to perform on each rotation cycle thus allowing multiple pill bottles to be processed in parallel in a pipelined manner in order to reduce the overall time of verification of multiple filled prescriptions.

The invention performs prescription quality control preferably using the technique of decision fusion. Given the different local decisions about the correctness of the content of the pill bottle, an inference system is designed to perform decision fusion so that the likelihood of the overall decision about the correct association of the content of the pill bottle with the prescription order is maximized.

Although this preferred embodiment of the present invention has been disclosed for illustrative purposes, those skilled in the art will appreciate that various modifications, additions and substitutions are possible, without departing from the scope and spirit of the invention as disclosed in the accompanying claims. It is also possible that other benefits or uses of the currently disclosed invention will become apparent over time.

What is claimed is:

1. An apparatus for verifying accuracy of a filled prescription of pills in a pill bottle, comprising:
an image acquisition apparatus which obtains image data associated with said pills in said pill bottle when said pill bottle is placed in a predetermined position;
a scale which obtains weight data associated with said pills in said pill bottle;
a prescription decision processor which determines a level of accuracy of said filled prescription of pills in said pill bottle based on said image data, said weight data, prescription information associated with said prescription associated with said pill bottle, and expected image information and expected weight information determined based on said prescription information.

2. An apparatus in accordance with claim 1, comprising;
a conveying mechanism which conveys said pill bottle to each of said image acquisition apparatus and said scale for obtaining said image data and said weight data respectively.

3. An apparatus in accordance with claim 2, wherein:
said image acquisition apparatus obtains image information from a first pill bottle and said scale obtains weight information from a second pill bottle simultaneously.

4. An apparatus in accordance with claim 1, comprising:
a range sensor which obtains a range measurement between said range sensor and a predefined area of said pill bottle or contents of said pill bottle when said pill bottle is positioned in said predetermined position.

5. An apparatus in accordance with claim 4, wherein:
said image acquisition apparatus comprises a camera having a camera lens; and
said camera utilizes said range measurement as a focal length between said lens and said pill bottle positioned in said predetermined position when said image acquisition apparatus obtains said image data.

6. An apparatus in accordance with claim 4, wherein:
said image acquisition apparatus utilizes said range measurement to position said image acquisition apparatus prior to obtaining said image data.

7. An apparatus in accordance with claim 4, wherein:
said prescription decision processor utilizes said range measurement to determine a volume of contents of said pill bottle present in said pill bottle for use in determining said level of accuracy of said filled prescription of pills in said pill bottle.

8. An apparatus in accordance with claim 4, comprising:
a conveying mechanism which conveys said pill bottle to each of said range sensor, said image acquisition apparatus, and said scale for obtaining said range measurement, said image data, and said weight data respectively.

9. An apparatus in accordance with claim 4, wherein:
said range sensor obtains a range measurement from a first pill bottle and said image acquisition apparatus obtains image information from a second pill bottle and said scale obtains weight information from a third pill bottle simultaneously.

10. An apparatus in accordance with claim 1, wherein:
said prescription decision processor comprises:
 a local image based decision engine that determines an image accuracy level decision based on said image data and said expected image information;
 a local weight based decision engine that determines a weight accuracy level decision based on said weight data and said expected weight information; and
a decision fusion inference engine that determines an overall prescription accuracy level decision based on said image accuracy level decision and said weight accuracy level decision.

11. An apparatus in accordance with claim 10, wherein:
said local image based decision engine classifies image information about contents of said pill bottle into at least one of a plurality of image based classes.

12. An apparatus in accordance with claim 10, wherein:
said local weight based decision engine classifies weight information about contents of said pill bottle into at least one of a plurality of weight based classes.

13. An apparatus in accordance with claim 10, wherein:
said decision fusion inference engine that classifies said filled prescription into at least one of a plurality of prescription accuracy levels.

14. An apparatus in accordance with claim 10, wherein:
said local image based decision engine classifies image information about contents of said pill bottle into at least one of a plurality of image based classes; and
said local weight based decision engine classifies weight information about contents of said pill bottle into at least one of a plurality of weight based classes.

15. An apparatus in accordance with claim 14, wherein:
said decision fusion inference engine classifies said filled prescription into at least one of a plurality of prescription accuracy levels.

16. A method for verifying accuracy of a filled prescription of pills in a pill bottle, said method comprising:
receiving actual image information about a filled prescription of pills in a pill bottle;
receiving actual weight information about a filled prescription of pills in a pill bottle;
determining a prescription accuracy level based on said actual image information and/or said actual weight information in view of expected image information and/or expected weight information respectively that is associated with said filled prescription of pills.

17. A method in accordance with claim 16, wherein said image information comprises a pill color of said pills in said pill bottle and/or a pill label on said pills in said pill bottle.

18. A method for verifying accuracy of a filled prescription of pills in a pill bottle, said method comprising:
positioning said pill bottle in a predetermined position;
reading prescription information from a prescription identifier on said pill bottle;
obtaining expected image information and expected weight information associated with said prescription information;
receiving actual image information about said filled prescription of pills in said pill bottle;
receiving actual weight information about said filled prescription of pills in said pill bottle;
determining a prescription accuracy level based on said actual image information and said actual weight information in view of said expected image information and expected weight information associated with said prescription information.

19. A method in accordance with claim 18, wherein said prescription information comprises one or more of a pill identifier, an ordered quantity of pills, a single pill weight associated with a single pill of a type indicated by said pill identifier, a pill color, and a pill label.

20. A method for performing quality control on a filled prescription of pills in a pill bottle, said method comprising the steps of:
receiving actual image information about said filled prescription of pills in said pill bottle;
obtaining expected image information about said filled prescription of pills in said pill bottle;
determining an image test accuracy level of said filled prescription based on said actual image information relative to said expected image information;
receiving actual weight information about said filled prescription of pills in said pill bottle;
obtaining expected weight information about said filled prescription of pills in said pill bottle;
determining a weight test accuracy level of said filled prescription based on said actual image information relative to said expected image information;
determining a prescription accuracy level based on said image test accuracy level and said weight test accuracy level.

* * * * *

UNITED STATES PATENT AND TRADEMARK OFFICE
CERTIFICATE OF CORRECTION

PATENT NO. : 7,028,723 B1 Page 1 of 1
APPLICATION NO. : 10/979474
DATED : April 18, 2006
INVENTOR(S) : Ali Tahar Alouani and Kenneth R. Currie It is certified that error appears in the above-identified patent and that said Letters Patent is hereby corrected as shown below:

Please Insert Item [76],
Middle name of first named inventor is misspelled. It should read: Ali Tahar Alouani Signed and Sealed this Twenty-fifth Day of July, 2006

JON W. DUDAS
*Director of the United States Patent and Trademark Office*